US009775226B1

(12) United States Patent
Bezel et al.

(10) Patent No.: US 9,775,226 B1
(45) Date of Patent: Sep. 26, 2017

(54) METHOD AND SYSTEM FOR GENERATING A LIGHT-SUSTAINED PLASMA IN A FLANGED TRANSMISSION ELEMENT

(71) Applicant: KLA-Tencor Corporation, Milpitas, CA (US)

(72) Inventors: Ilya Bezel, Sunnyvale, CA (US); Anatoly Shchemelinin, Pleasanton, CA (US); Matthew Derstine, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/231,196

(22) Filed: Mar. 31, 2014

Related U.S. Application Data

(60) Provisional application No. 61/806,719, filed on Mar. 29, 2013.

(51) Int. Cl.
*A61N 5/06* (2006.01)
*H05H 1/24* (2006.01)

(52) U.S. Cl.
CPC .................................... *H05H 1/24* (2013.01)

(58) Field of Classification Search
CPC ........ G01N 21/718; G01N 21/73; H05G 2/00; H05G 2/001; H05G 2/008
USPC .................... 250/504 R, 492.1, 492.2, 492.3
See application file for complete search history.

(56) References Cited

U.S. PATENT DOCUMENTS 3,619,588 A * 11/1971 Chambers .............. G01N 21/63 359/859
4,031,424 A * 6/1977 Penfold ............... H01J 37/3402 204/192.12
4,229,780 A * 10/1980 Nelson .................... F21V 25/12 362/218
5,155,336 A * 10/1992 Gronet .................. C23C 16/481 219/390
6,414,436 B1 7/2002 Eastlund et al.
7,705,331 B1 4/2010 Kirk et al.
8,054,000 B2 11/2011 Mizojiri et al.
8,409,353 B2 4/2013 Yokota et al.
(Continued)

FOREIGN PATENT DOCUMENTS

EP 1296355 A2 3/2003
EP 1470569 10/2004
WO 03030212 A1 4/2003

*Primary Examiner* — Jason McCormack
(74) *Attorney, Agent, or Firm* — Suiter Swantz pc llo

(57) ABSTRACT

A system for forming a light-sustained plasma capable of emitting vacuum ultraviolet light includes an illumination source configured to generate illumination, a plasma cell including a transmission element having one or more openings, one or more flanges disposed at the openings of the transmission element and configured to enclose the internal volume of the transmission element in order to contain a volume of gas within the plasma cell. The system further includes a collector element arranged to focus the illumination from the illumination source into the volume of gas to generate a plasma within the volume of gas contained within the plasma cell. Further, the plasma emits broadband radiation including at least vacuum ultraviolet radiation. In addition, the transmission element of the plasma cell is transparent to the illumination generated by the illumination source and at least the vacuum ultraviolet radiation emitted by the plasma.

46 Claims, 7 Drawing Sheets

(56) References Cited

U.S. PATENT DOCUMENTS

| | | | | |
|---|---|---|---|---|
| 2007/0046167 | A1* | 3/2007 | Lantis | H01J 5/48 313/311 |
| 2007/0228288 | A1 | 10/2007 | Smith | |
| 2007/0228300 | A1 | 10/2007 | Smith | |
| 2011/0181191 | A1* | 7/2011 | Smith | B82Y 10/00 315/149 |
| 2011/0254449 | A1* | 10/2011 | Murnick | H01J 63/02 315/111.81 |
| 2012/0019133 | A1* | 1/2012 | Graham | H01J 61/0732 313/573 |
| 2012/0146497 | A1* | 6/2012 | Stockwald | H01J 61/30 313/631 |

* cited by examiner

METHOD AND SYSTEM FOR GENERATING A LIGHT-SUSTAINED PLASMA IN A FLANGED TRANSMISSION ELEMENT

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional Patent Application entitled CRYSTALLINE CELL FOR LASER SUSTAINED PLASMA SOURCE, naming Ilya Bezel, Anatoly Shchemelinin and Matthew Derstine as inventors, filed Mar. 29, 2013, Application Ser. No. 61/806,719.

TECHNICAL FIELD

The present invention generally relates to plasma based light sources, and, more particularly, to a plasma cell capable of generating and emitting short-wavelength radiation, such as vacuum ultraviolet radiation.

BACKGROUND

As the demand for integrated circuits having ever-small device features continues to increase, the need for improved illumination sources used for inspection of these ever-shrinking devices continues to grow. One such illumination source includes a laser-sustained plasma source. Laser-sustained plasma light sources are capable of producing high-power broadband light. Laser-sustained light sources operate by focusing laser radiation into a gas volume in order to excite the gas, such as argon or xenon, into a plasma state, which is capable of emitting light. This effect is typically referred to as "pumping" the plasma. Bulbs utilized in traditional plasma-based light sources are commonly made from fused silica glass. Fused silica glass generally absorbs light having wavelengths shorter than approximately 190 nm. This absorption of short-wavelength light causes rapid degradation of the optical transmission capabilities of the fused silica glass bulb in spectral ranges including 190-260 nm and leads to overheating and even explosion of the bulb, thereby limiting the usefulness of powerful laser sustained plasma sources in the range of 190-260 nm. Therefore, it would be desirable to provide a system and method for curing defects such as those of the identified above.

SUMMARY

A system for forming a light-sustained plasma is disclosed, in accordance with an illustrative embodiment of the present invention. In one embodiment, the system may include an illumination source configured to generate illumination. In another embodiment, the system may include a plasma cell including a transmission element having one or more openings. In another embodiment, the system may include one or more flanges disposed at the one or more openings of the transmission element and configured to enclose the internal volume of the transmission element in order to contain a volume of gas within the plasma cell. In another embodiment, the system may include a collector element arranged to focus the illumination from the illumination source into the volume of gas in order to generate a plasma within the volume of gas contained within the plasma cell. In another embodiment, the plasma emits broadband radiation including at least vacuum ultraviolet radiation. In another embodiment, the transmission element of the plasma cell is at least partially transparent to at least a portion of the illumination generated by the illumination source and at least a portion of the vacuum ultraviolet radiation emitted by the plasma.

In another illustrative embodiment, the system may include an illumination source configured to generate illumination. In another embodiment, the system may include a plasma cell including a transmission element having one or more openings. In another embodiment, the system may include one or more removable flanges disposed at the one or more openings of the transmission element and configured to enclose the internal volume of the transmission element in order to contain a volume of gas within the plasma cell. In another embodiment, the system may include a collector element arranged to focus the illumination from the illumination source into the volume of gas in order to generate a plasma within the volume of gas, whereby the plasma emits broadband radiation. In another embodiment, the transmission element of the plasma cell is at least partially transparent to at least a portion of the illumination generated by the illumination source and at least a portion of the broadband radiation emitted by the plasma.

A plasma cell for forming a light-sustained plasma is disclosed, in accordance with an illustrative embodiment of the present invention. In one embodiment, the plasma cell may include a transmission element having one or more openings. In another embodiment, the plasma cell includes one or more flanges disposed at the one or more openings of the transmission element and configured to enclose the internal volume of the transmission element in order to contain a volume of gas within the transmission element. In another embodiment, the transmission element is configured to receive illumination from an illumination source in order to generate a plasma within the volume of gas. In another embodiment, the plasma emits broadband radiation including at least vacuum ultraviolet (VUV) radiation. In another embodiment, the transmission element of the plasma cell is at least partially transparent to at least a portion of the illumination generated by the illumination source and at least a portion of the VUV radiation emitted by the plasma.

A method for forming a light-sustained plasma is disclosed, in accordance with an illustrative embodiment of the present invention. In one embodiment, the method may include generating illumination; containing a volume of gas within a plasma cell; focusing at least a portion of the generated illumination through a transmission element of the plasma cell into the volume of gas contained within the plasma cell; generating broadband radiation including at least vacuum ultraviolet radiation by forming a plasma via absorption of the focused generated illumination by at least a portion of the volume of gas contained within the plasma cell; and transmitting at least a portion of the vacuum ultraviolet radiation through the transmission element of the plasma cell.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Figure 1A:
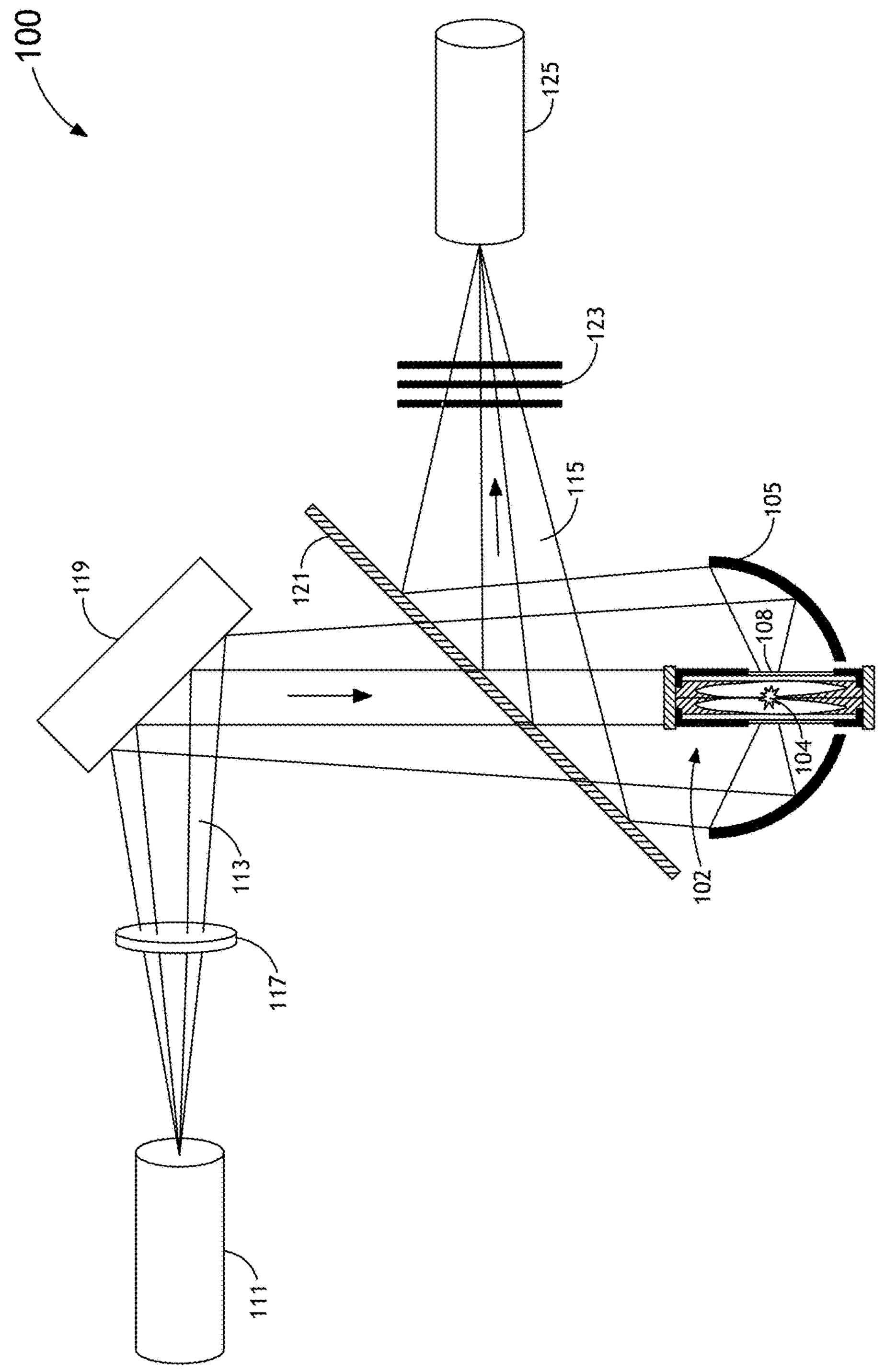
FIG. 1A is a high level schematic view of a system for forming a light-sustained plasma, in accordance with one embodiment of the present invention.
Figure 1C:
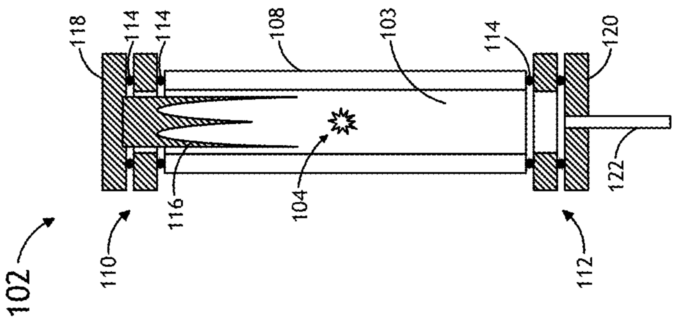
FIG. 1C is a high level schematic view of a plasma cell, in accordance with one embodiment of the present invention.
Figure 1B:
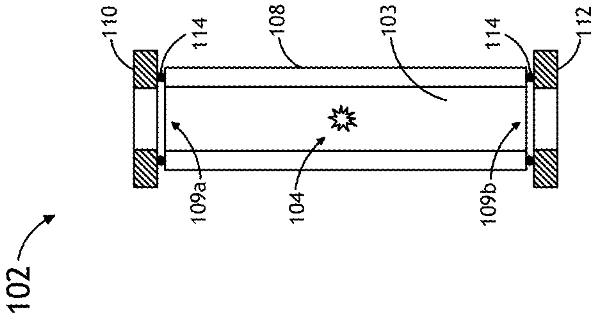
FIG. 1B is a high level schematic view of a plasma cell, in accordance with one embodiment of the present invention.
Figure 1D:
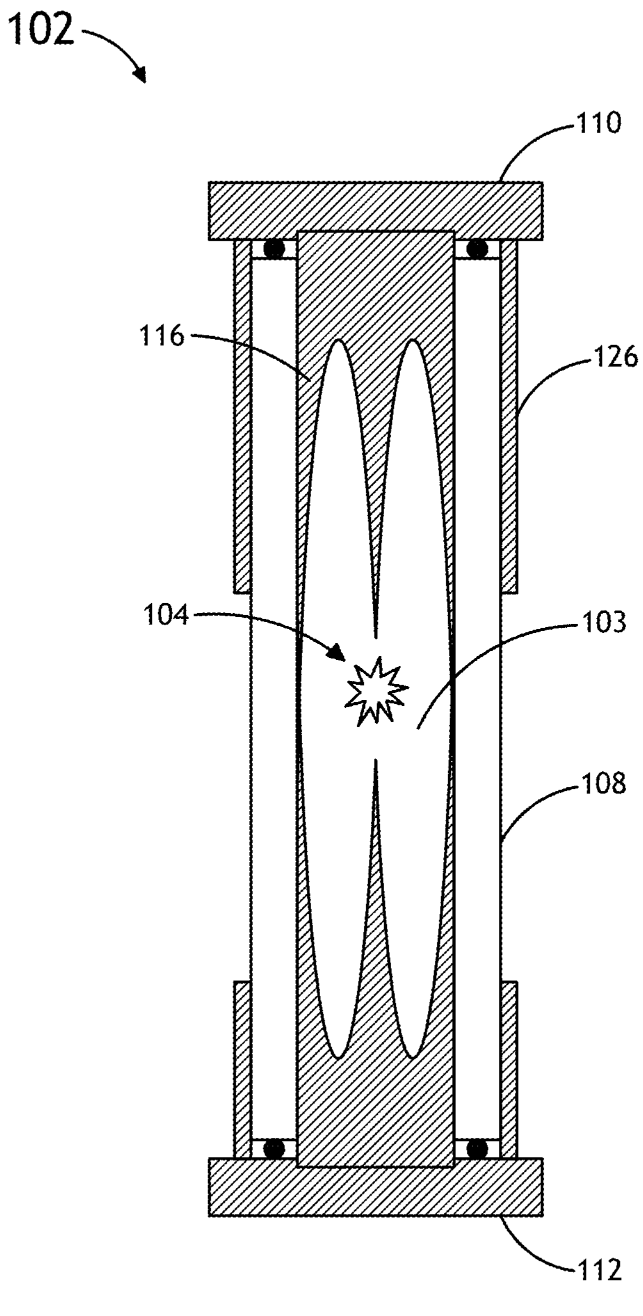
FIG. 1D is a high level schematic view of a plasma cell equipped with one or more radiation shields, in accordance with one embodiment of the present invention.
Figure 1F:
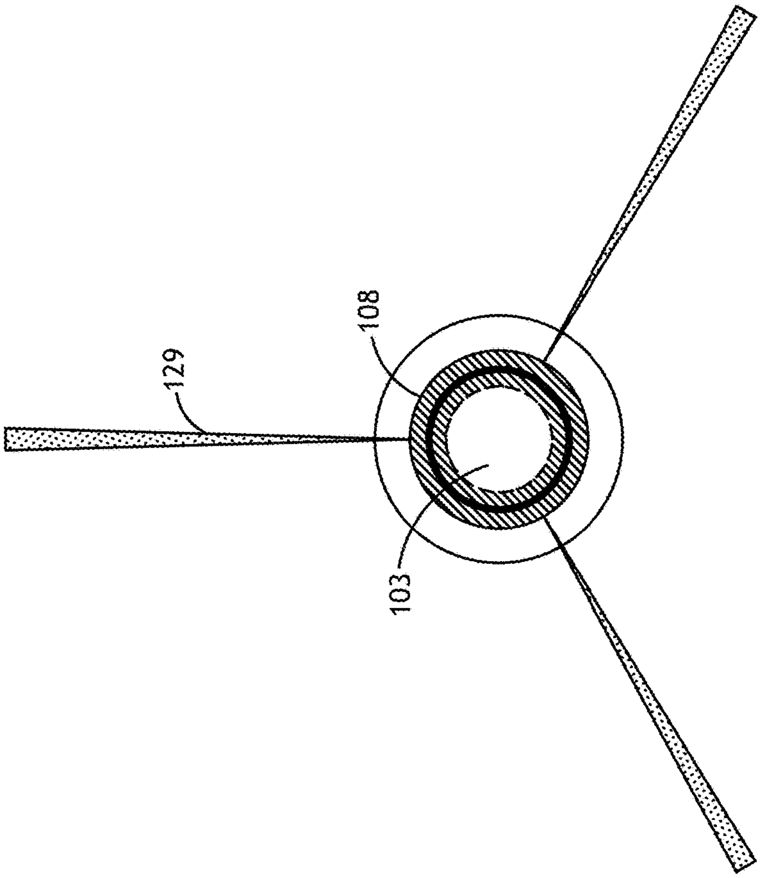
FIG. 1F is a high level schematic view of a plasma cell equipped with one or more fins, in accordance with one embodiment of the present invention.
Figure 1E:
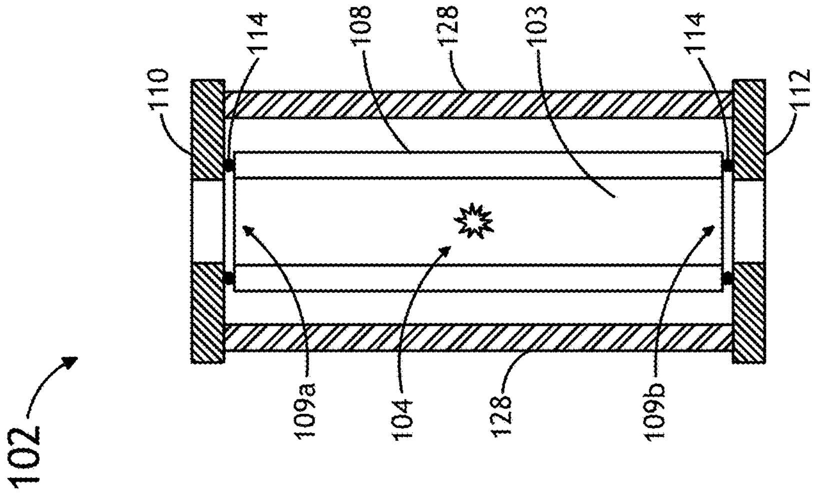
FIG. 1E is a high level schematic view of a plasma cell equipped with one or more connecting rods, in accordance with one embodiment of the present invention.
Figure 1G:
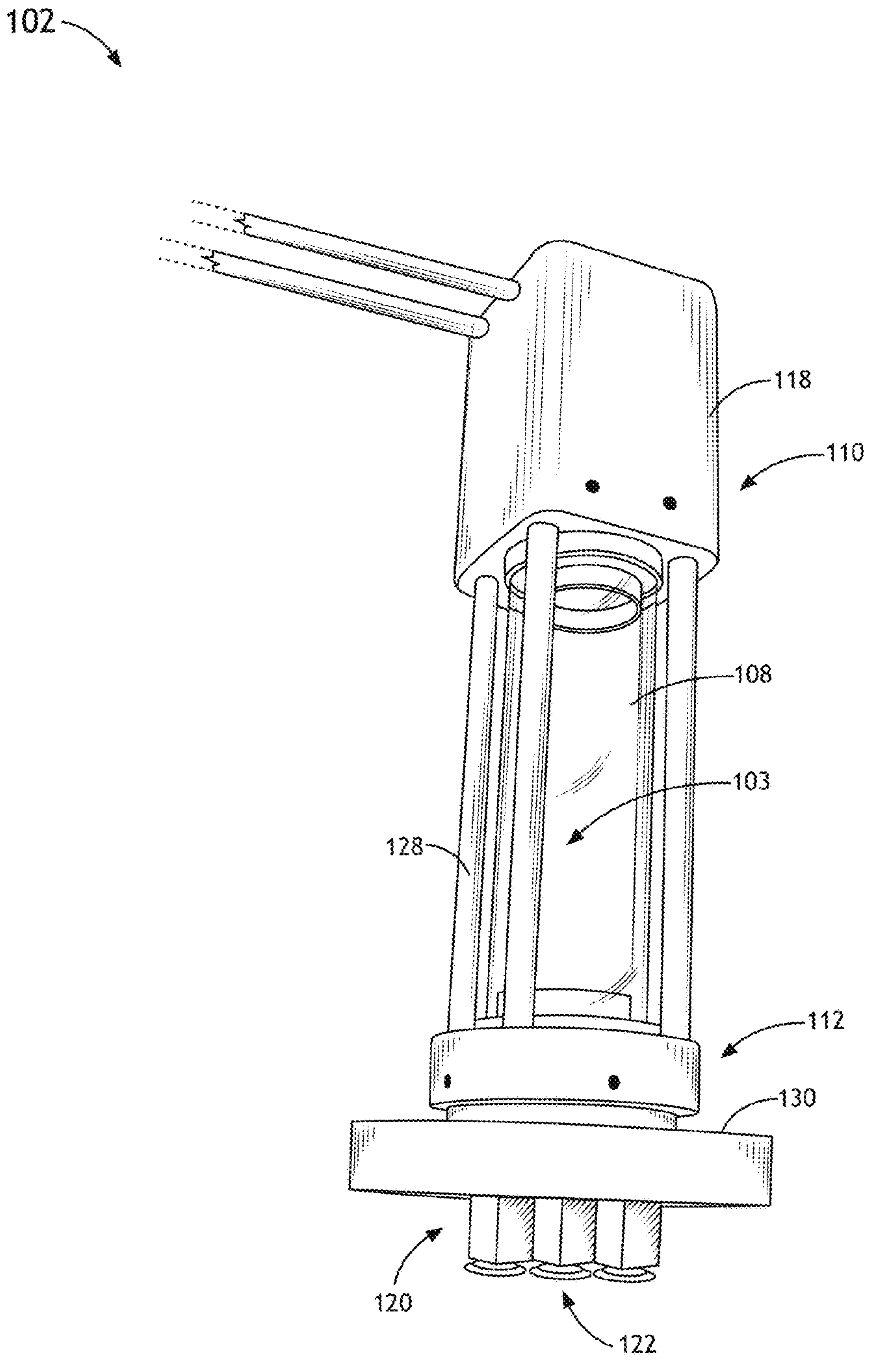
FIG. 1G is a perspective view of a plasma cell of a system for forming a light-sustained plasma, in accordance with one embodiment of the present invention.
Figure 1H:
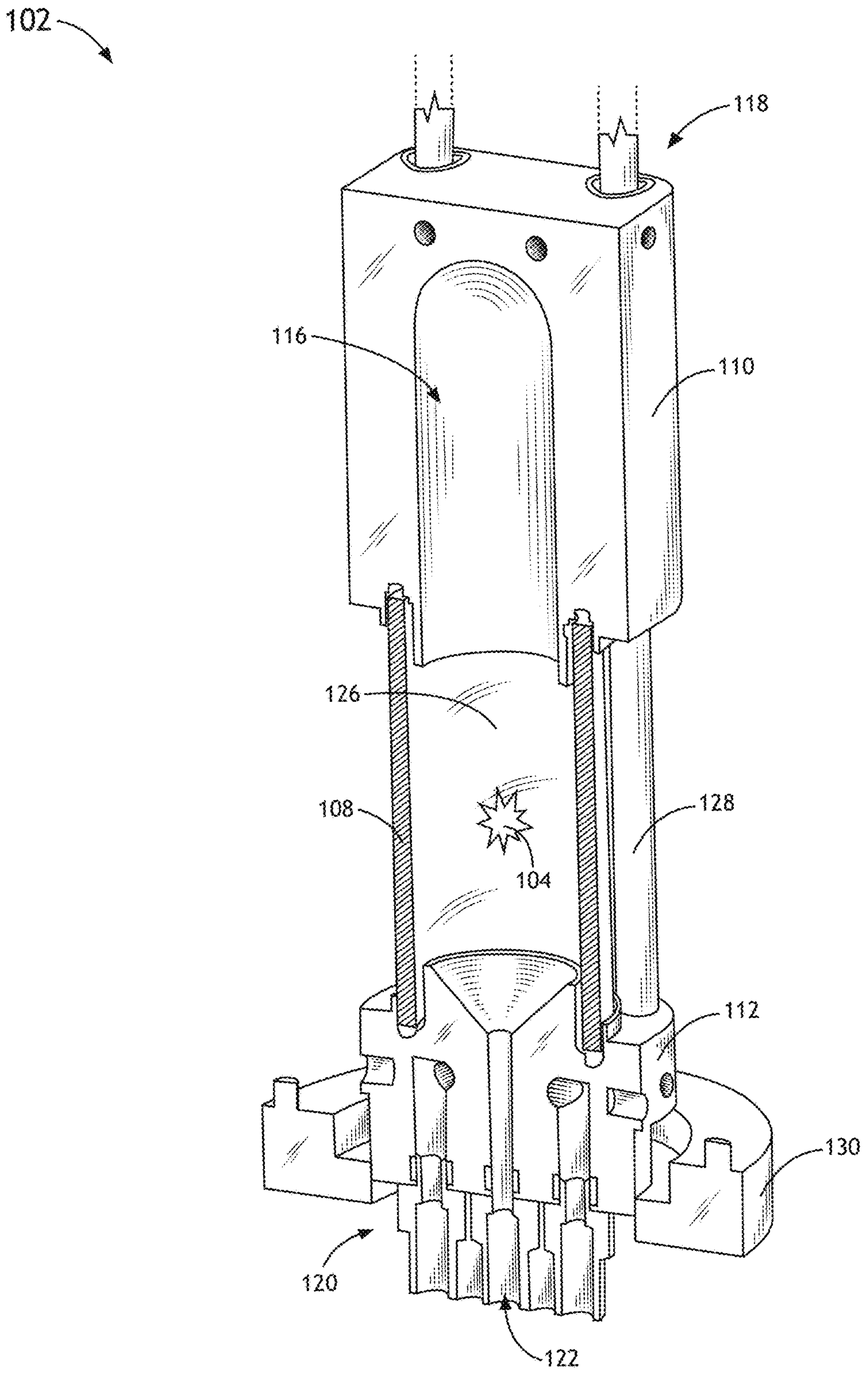
FIG. 1H is a cross-sectional view of a plasma cell of a system for forming a light-sustained plasma, in accordance with one embodiment of the present invention.
Figure 2:
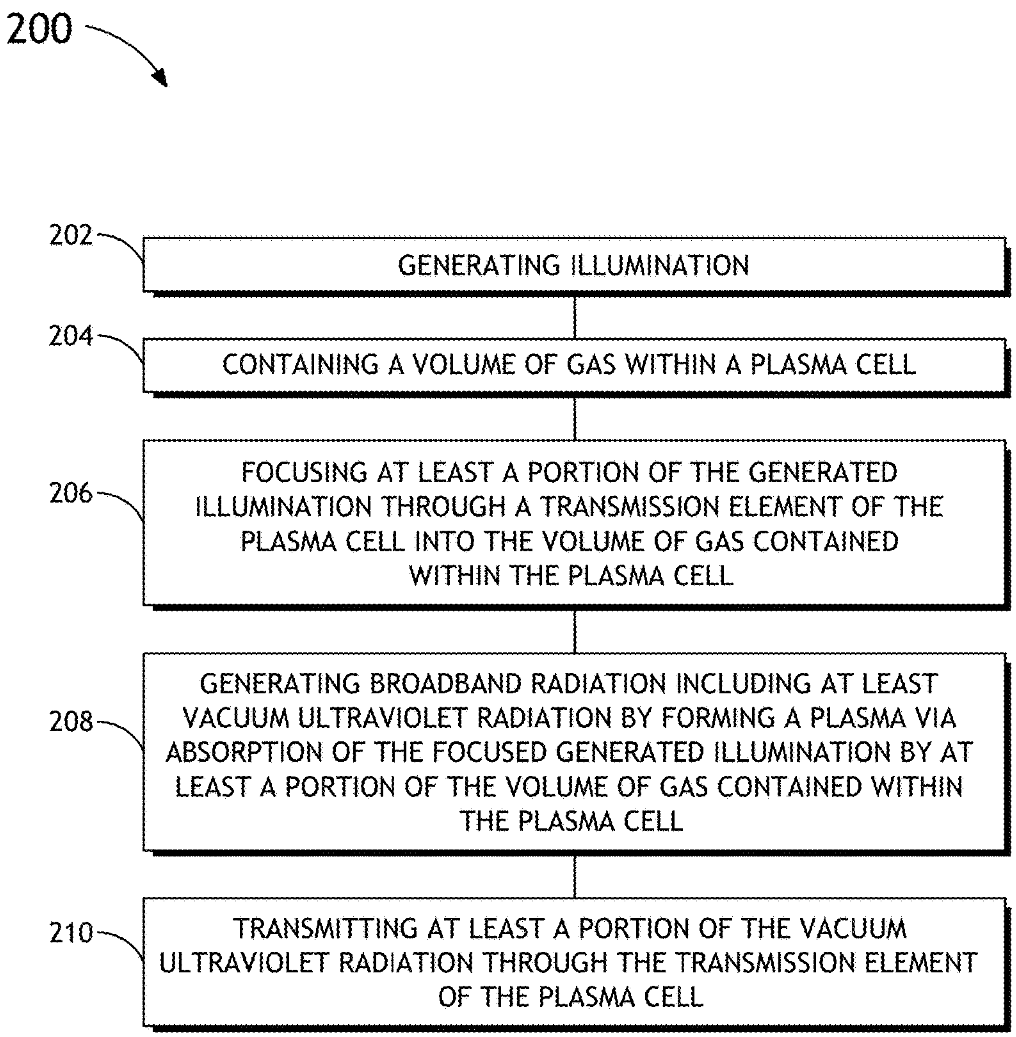
FIG. 2 is a flow diagram illustrating a method for forming a light-sustained plasma, in accordance with one embodiment of the present invention.

Referring generally to FIGS. 1A through 2, a system and method for generating a light-sustained plasma suitable for emitting short-wavelength radiation are described in accordance with the present disclosure. Some embodiments of the present invention are directed to the generation of broadband light, which may include vacuum ultraviolet radiation, with a light-sustained plasma light source. Some embodiments of the present invention provide a plasma cell equipped with a transmission element that is transparent to both the pumping light (e.g., light from a laser source) used to sustain a plasma within the plasma cell and broadband light (e.g., VUV light, DUV light, UV light and/or visible light) emitted by the plasma. Some embodiments of the present invention provide various control elements (e.g., temperature control, convective control and the like) and/or protective elements (e.g., radiation shield and the like) that are coupled to, or integrated with, one or more portions of the plasma cell, such as one or more flanges (e.g., metal flanges or ceramic flanges), which serve to terminate openings of the transmission element of the plasma cell.

FIGS. 1A-1F illustrate a system 100 for forming a light-sustained plasma suitable for emitting short-wavelength radiation, in accordance with one embodiment of the present invention. The generation of plasma within inert gas species is generally described in U.S. patent application Ser. No. 11/695,348, filed on Apr. 2, 2007; and U.S. patent application Ser. No. 11/395,523, filed on Mar. 31, 2006, which are incorporated herein in their entirety. Various plasma cell designs and plasma control mechanisms are described in U.S. patent application Ser. No. 13/647,680, filed on Oct. 9, 2012, which is incorporated herein by reference in the entirety. The generation of plasma is also generally described in U.S. patent application Ser. No. 14/224,945, filed on Mar. 25, 2014, which is incorporated by reference herein in the entirety.

In one embodiment, the system 100 includes an illumination source 111 (e.g., one or more lasers) configured to generate illumination of a selected wavelength, or wavelength range, such as, but not limited to, infrared radiation. In another embodiment, the system 100 includes a plasma cell 102 for generating, or maintaining, a plasma 104. In another embodiment, the plasma cell 102 includes a transmission element 108. In another embodiment, the transmission element 108 may have one or more openings 109. In another embodiment, one or more flanges 110, 112 are disposed at the one or more openings 109*a*, 109*b* of the transmission element 108. In one embodiment, the one or more flanges 110, 112 are configured to enclose the internal volume of the transmission element 108 so as to contain a volume of gas 103 within the body of the transmission element 108 of the plasma cell 102. In one embodiment, the one or more openings 109*a*, 109*b* may be located at one or more end portions of the transmission element 108. For example, as shown in FIGS. 1B-1E, a first opening 109*a* may be located at a first end portion of the transmission element 108, while a second opening 109*b* may be located at a second end portion, opposite of the first end portion, of the transmission element 108. In another embodiment, the one or more flanges 110, 112 are arranged to terminate the transmission element 108 at the one or more end portions of the transmission element 108, as shown in FIGS. 1B-1E. For example, a first flange 110 may be positioned to terminate the transmission element 108 at the first opening 109*a*, while the second flange 112 may be positioned to terminate the transmission element 108 at the second 109*b*. In another embodiment, the first opening 109*a* and the second opening 109*b* are in fluidic communication with one another such that the internal volume of the transmission element 108 is continuous from the first opening 109*a* to the second opening 109*b*.

In another embodiment, as shown in FIGS. 1B-1E, the plasma cell 102 includes one or more seals 114. In one embodiment, the seals 114 are configured to provide a seal between the body of the transmission element 108 and the one or more flanges 110, 112 coupled to the transmission element 108. In another embodiment, as shown in FIG. 1C, the seals 114 are configured to provide a seal between a first portion of the one or more flanges 110, 112 and an additional portion of the one or more flanges 110, 112. For example, the seals 114 may provide a seal between a portion of the one or more flanges 110, 112 coupled to an end portion of the transmission element 108 and an additional portion of the one or more flanges 110, 112 (e.g., top cooling element 118/bottom cooling element 120). The seals 114 of the plasma cell 102 may include any seals known in the art. For example, the seals 114 may include, but are not limited to, a brazing, an elastic seal, an O-ring, a C-ring, a metal seal and the like. In one embodiment, the seals 114 may include one or more soft metal alloys, such as an indium-based alloy. In another embodiment, the seals 114 may include an indium-coated C-ring.

In one embodiment, the transmission element 108 may contain any selected gas (e.g., argon, xenon, mercury or the like) known in the art suitable for generating a plasma upon absorption of suitable illumination. In one embodiment, focusing illumination 113 from the illumination source 111 into the volume of gas 103 causes energy to be absorbed through one or more selected absorption lines of the gas or plasma 104 within the transmission element 108, thereby "pumping" the gas species in order to generate or sustain a plasma 104. In another embodiment, although not shown, the plasma cell 102 may include a set of electrodes for initiating the plasma 104 within the internal volume 103 of the transmission element 108, whereby the focusing illumination 113 from the illumination source 111 maintains the plasma 104 after ignition by the electrodes.

In another embodiment, the system 100 includes a collector/reflector element 105 (e.g., an ellipsoid-shaped collector element) configured to focus illumination 113 emanating from the illumination source 111 into the volume of gas 103 contained within the transmission element 108 of the plasma cell 102. The collector element 105 may take on any physical configuration known in the art suitable for focusing illumination 113 emanating from the illumination source 111 into the volume of gas 103 contained within the transmission element 108 of the plasma cell 102. In one embodiment, as shown in FIG. 1A, the collector element 105 may include a concave region with a reflective internal surface suitable for receiving illumination 113 from the illumination source 111 and focusing the illumination 113 into the volume of gas 103 contained within the transmission element 108. For example, the collector element 105 may include an ellipsoid-shaped collector element 105 having a reflective internal surface, as shown in FIG. 1A.

In another embodiment, the plasma 104 generated, or maintained, within the volume 103 of the transmission element 108 emits broadband radiation. In one embodiment, the broadband illumination 115 emitted by the plasma 104 includes at least vacuum ultraviolet (VUV) radiation. In another embodiment, the broadband illumination 115 emitted by the plasma 104 includes deep ultraviolet (DUV) radiation. In another embodiment, the broadband illumination 115 emitted by the plasma 104 includes ultraviolet (UV) radiation. In another embodiment, the broadband illumination 115 emitted by the plasma 104 includes visible radiation. For example, the plasma 104 may emit short-wavelength radiation in the range of 120 to 200 nm. In this regard, the transmission element 108 allows the plasma cell 102 of system 100 to serve as a VUV radiation source. In another embodiment, the plasma 104 may emit short-wavelength radiation having a wavelength below 120 nm. In another embodiment, the plasma 104 may emit radiation having a wavelength larger than 200 nm.

The transmission element 108 of system 100 may be formed from any material known in the art that is at least partially transparent to radiation generated by plasma 104. In one embodiment, the transmission element 108 of system 100 may be formed from any material known in the art that is at least partially transparent to VUV radiation generated by plasma 104. In another embodiment, the transmission element 108 of system 100 may be formed from any material known in the art that is at least partially transparent to DUV radiation generated by plasma 104. In another embodiment, the transmission element 108 of system 100 may be formed from any material known in the art that is transparent to UV light generated by plasma 104. In another embodiment, the transmission element 108 of system 100 may be formed from any material known in the art transparent to visible light generated by plasma 104.

In another embodiment, the transmission element 108 may be formed from any material known in the art transparent to illumination 113 (e.g., IR radiation) from the illumination source 111.

In another embodiment, the transmission element 108 may be formed from any material known in the art transparent to both illumination 113 from the illumination source 111 (e.g., IR source) and broadband illumination 115 (e.g., VUV radiation, DUV radiation, UV radiation, and visible radiation) emitted by the plasma 104 contained within the volume 103 of the transmission element 108.

For example, the transmission element 108 may include, but is not limited to, calcium fluoride ($CaF_2$), magnesium fluoride ($MgF_2$), crystalline quartz and sapphire, which are capable of transmitting VUV radiation (from the plasma 104) and laser radiation (e.g., infrared radiation) from the illumination source 111. It is noted herein that materials such as, but not limited to, $CaF_2$, $MgF_2$, crystalline quartz and sapphire provide transparency to radiation with wavelength shorter than 190 nm. For instance, $CaF_2$ is transparent to radiation having a wavelength as short as approximately 120 nm. Further, these materials are resistant to rapid degradation when exposed to short-wavelength radiation, such as VUV radiation. By way of another example, in some instances, fused silica may be utilized to form the transmission element 108. It is noted herein that fused silica does provide some transparency to radiation having wavelength shorter than 190 nm, showing useful transparency to wavelengths as short as 170 nm.

In another embodiment, the collector element 105 is arranged to collect broadband illumination 115 (e.g., VUV radiation, DUV radiation, UV radiation and/or visible radiation) emitted by plasma 104 and direct the broadband illumination 115 to one or more additional optical elements (e.g., filter 123, homogenizer 125, and the like). For example, the collector element 105 may collect at least VUV broadband illumination 115 emitted by plasma 104 and direct the broadband illumination 115 to one or more downstream optical elements. By way of another example, the collector element 105 may collect DUV broadband illumination 115 emitted by plasma 104 and direct the broadband illumination 115 to one or more downstream optical elements. By way of another example, the collector element 105 may collect UV broadband illumination 115 emitted by plasma 104 and direct the broadband illumination 115 to one or more downstream optical elements. By way of another example, the collector element 105 may collect visible broadband illumination 115 emitted by plasma 104 and direct the broadband illumination 115 to one or more downstream optical elements. In this regard, the plasma cell 102 may deliver VUV radiation, UV radiation, and/or visible radiation to downstream optical elements of any optical characterization system known in the art, such as, but not limited to, an inspection tool or a metrology tool. It is noted herein the plasma cell 102 of system 100 may emit useful radiation in a variety of spectral ranges including, but not limited to, DUV radiation, VUV radiation, UV radiation, and visible radiation. Further, it is noted herein that the system 100 may utilize any of these radiation bands, while mitigating damage caused to the transmission element 108 by the VUV radiation. In this regard, the transmission element 108 may be formed from a material that is resistant to VUV light, even in cases where the primary purpose of the system 100 does not include the utilization of the VUV light.

The transmission element 108 may take on any shape known in the art. In one embodiment, the transmission element 108 may have a cylindrical shape, as shown in FIGS. 1B-1E. In another embodiment, although not shown, the transmission element 108 may have a spherical shape. In another embodiment, although not shown, the transmission element 108 may have a composite shape. For example, the shape of the transmission element 108 may consist of a combination of two or more shapes. For instance, the shape of the transmission element 108 may consist of a spherical center portion, arranged to contain the plasma 104, and one or more cylindrical portions extending above and/or below the spherical center portion, whereby the one or more cylindrical portions are coupled to the one or more flanges 110,112.

In the case where the transmission element 108 is cylindrically shaped, as shown in FIG. 1B, the one or more openings 109*a*, 109*b* may be located at one or more end portions of the cylindrically shaped transmission element 108. In this regard, the transmission element 108 takes the form of a hollow cylinder, whereby a channel extends from the first opening 109*a* to the second opening 109*b*. In another embodiment, the first flange 110 and the second flange 112 together with the wall(s) of the transmission element 108 serve to contain the volume of gas 103 within the channel of the transmission element 108. It is recognized herein that this arrangement may be extended to a variety of transmission element 108 shapes, as described previously herein.

Referring again to FIGS. 1C through 1D, the one or more flanges 110, 112 may include one or more control elements. In one embodiment, the one or more the one or more flanges 110, 112 may include one or more control elements for controlling one or more characteristics of the plasma cell 102, the transmission element 108, the gas within volume 103, the plasma 104 and/or a plume from the plasma.

In one embodiment, the one or more control elements of the one or more flanges 110, 112 may include an internal control element. For example, the one or more control elements of the one or more flanges 110, 112 may include an internal control element located within the internal volume of the transmission element 108. In one embodiment, the one or more control elements of the one or more flanges 110, 112 may include an external control element. For example, the one or more control elements of the one or more flanges 110, 112 may include an external control element mounted to a surface of the one or more flanges 110, 112 that is external to the internal volume of the transmission element 108.

In one embodiment, as shown in FIG. 1C, the one or more flanges 110, 112 may include a temperature control element. For example, the temperature control element may be disposed inside or outside of the transmission element 108 of the plasma cell 102. The temperature control element may include any temperature control element known in the art used to control the temperature of the plasma cell 102, the plasma 104, the gas within volume 103, the transmission element 108, the one or more flanges 110,112, and/or the plasma plume (not shown).

In one embodiment, the temperature control element may be utilized to cool the plasma cell 102, transmission element 108, the plasma 104, the flanges 110,112 and/or the plume of the plasma by transferring thermal energy to a medium external to the transmission element 108. In one embodiment, the temperature control element may include, but is not limited to, a cooling element for cooling plasma cell 102, transmission element 108, the plasma 104, the gas within volume 103, the flanges 110,112, and/or the plume of the plasma. For example, as shown in FIG. 1C, the one or more flanges 110, 112 may include one or more water cooling elements 118, 120.

In another embodiment, the one or more flanges 110, 112 may include one or more passive heat transfer elements coupled to one or more portions of the one or more flanges 110, 112. For example, the one or more passive heat transfer elements may include, but are not limited to, baffles, chevrons or fins arranged to transfer thermal energy from the hot plasma 104 to a portion of the plasma cell 102 (e.g., top electrode), the one or more flanges 110, 112 or the transmission element 108 to facilitate heat transfer out of the transmission element 108.

The utilization of heat transfer elements is generally described in U.S. patent application Ser. No. 13/647,680, filed on Oct. 9, 2012, which is incorporated by reference above in the entirety. The utilization of heat transfer elements is also generally described in U.S. patent application Ser. No. 12/787,827, filed on May 26, 2010, which is incorporated by reference herein in the entirety. The utilization of heat transfer elements is also generally described in U.S. patent application Ser. No. 14/224,945, filed on Mar. 25, 2014, which is incorporated by reference above in the entirety.

In another embodiment, the one or more flanges 110, 112 include one or more convection control elements. For example, a convection control element may be disposed inside or outside of the transmission element 108 of the plasma cell 102. The convection control element may include any convection control device known in the art used to control convection in the transmission element 108. For example, the convection control element may include one or more devices (e.g., structures mechanically coupled to one or more flanges 110,112 and positioned inside transmission element 108) suitable for controlling convection currents within the transmission element 108 of plasma cell 102. For instance, the one or more structures for controlling convection currents may be arranged within the transmission element 108 in a manner to impact the flow of hot gas from the hot plasma 104 of the plasma cell 102 to the cooler inner surfaces of the transmission element 108. In this regard, the one or more structures may be configured in a manner to direct convective flow to regions within the transmission element 108 that minimize or at least reduce damage to the wall of the transmission element 108 caused by the high temperature gas.

In another embodiment, the cooling elements described previously herein (e.g., water cooling elements 118, 120) may provide convection control, allowing the system 100 to capture, direct and/or dissipate the plasma plume.

The utilization of convection control devices is generally described in U.S. patent application Ser. No. 13/647,680, filed on Oct. 9, 2012, which is incorporated by reference above in the entirety. The utilization of convection control devices are also generally described in U.S. patent application Ser. No. 12/787,827, filed on May 26, 2010, which is incorporated by reference above in the entirety. The utilization of convection control devices is also generally described in U.S. patent application Ser. No. 14/224,945, filed on Mar. 25, 2014, which is incorporated by reference above in the entirety.

In another embodiment, as shown in FIGS. 1C and 1D, the one or more flanges 110, 112 may include one or more plume control devices 116. For example, the plume control device 116 may include a plume capture or redirection device coupled to the one or more flanges 110, 112 and positioned disposed inside of the transmission element 108 of plasma cell 102, as shown in FIGS. 1C and 1D. The plume control element may include any plume control device known in the art used to capture or redirect the plume of plasma 104 within the transmission element 108. For example, the plume control element may include one or more devices having a concave portion suitable for capturing and redirecting a convection plume emanating from the plasma region 104 within the transmission element 108 of the plasma cell 102. For instance, the plume control element may include one or more electrodes (e.g., top electrode) coupled to the internal surface of one or more flanges 110, 112 and positioned within the transmission element 108 of plasma cell 102 having a concave portion or a hollow portion suitable for capturing and/or redirecting a convection plume emanating from the plasma region 104 within the transmission element of the plasma cell 102. The utilization of plume control devices is generally described in U.S. patent application Ser. No. 13/647,680, filed on Oct. 9, 2012, which is incorporated by reference above in the entirety. The utilization of plume control devices is also generally described in U.S. patent application Ser. No. 12/787,827, filed on May 26, 2010, which is incorporated by reference above in the entirety. The utilization of plume control devices is also generally described in U.S. patent application Ser. No. 14/224,945, filed on Mar. 25, 2014, which is incorporated by reference above in the entirety.

In another embodiment, as shown in FIG. 1C, one or more removable flanges 110, 112 may include a gas fill control element 122. In one embodiment, the gas fill control element 122 includes a gas pipe or tube serving to fluidically couple a gas source and the transmission element 108. In another embodiment, the system 100 may include a gas valve positioned along the gas line (between the gas source and the transmission element 108), allowing a user to control the amount and type of gas contained within the transmission element 108. The utilization of gas fill devices is generally described in U.S. patent application Ser. No. 13/647,680, filed on Oct. 9, 2012, which is incorporated by reference above in the entirety.

In another embodiment, the one or more flanges 110, 112 may include one or more plasma ignition elements. For example, one or more electrodes may be mounted on the internal surface of one or more flanges 110, 112 and positioned within the internal volume of the transmission element 108. The utilization of various electrode configurations is generally described in U.S. patent application Ser. No. 13/647,680, filed on Oct. 9, 2012, which is incorporated by reference above in the entirety.

In another embodiment, as shown in FIG. 1D, the one or more flanges 110, 112 may include one or more radiation shield elements 126. In one embodiment, the radiation shielding elements 126 may include a radiation shield proximate to the one or more openings of the transmission element 108 configured to block radiation from at least one of the illumination source 111 and the radiation generated by the plasma 104 from reaching one or more seals 114 of the plasma cell 102. In one embodiment, the radiation shielding elements 126 may include a structure suitable for shielding one or more portions of the plasma cell 102 from radiation from the plasma 104 or from the illumination 113 from the light source 111 (e.g., radiation from laser).

In another embodiment, a coating material may be applied to one or more inside or outside portions of the transmission element 108 in order to block radiation from the plasma 104 from one or more selected portions of the plasma cell 102. In another embodiment, the plasma cell 102 may include a coating layer proximate to the one or more openings of the transmission element 108 configured to block at least a portion of the radiation generated by the plasma 104 from reaching one or more seals 114 of the plasma cell 102. For example, a coating material (e.g., metal material) may be applied to one or more inside or outside end portions of a cylindrical transmission element 108 in order to block radiation (e.g., UV radiation) from the plasma 104 from damaging (or at least limit damage) the seals 114. In another embodiment, an anti-reflective coating material may be applied to one or more inside or outside portions of the transmission element 108 in order to block radiation from the plasma 104 from one or more selected portions of the plasma cell 102. The utilization of radiation shields and radiation blocking coating layers is generally described in U.S. patent application Ser. No. 13/647,680, filed on Oct. 9, 2012, which is incorporated by reference above in the entirety.

In another embodiment, one or more flanges 110, 112 may include one or more sensors (not shown) configured to measure one or more characteristics (e.g., thermal characteristics, pressure characteristics, radiation characteristics and the like) of the plasma cell 102, the transmission element 108, the plasma 104, the gas within volume 103, the plume of the plasma 104 and the like. In one embodiment, the one or more sensors may include a sensor disposed on the outside or inside surface of one or more flanges 110, 112. For example, the one or more sensors may include, but are not limited to, a temperature sensor, a pressure sensor, a radiation sensor and the like.

FIG. 1E illustrates a simplified schematic diagram of the plasma cell 102 equipped with one or more connecting rods 128, in accordance with one or more embodiments of the present invention. In one embodiment, the one or more connecting rods 128 of the plasma cell 102 may serve to secure the one or more flanges 110, 112 at the openings 109*a*, 109*b*. In the case of a cylindrical transmission element 108, the connecting rods 128 may be coupled to a first flange 110 and a second flange 112 positioned on the opposite end of the transmission element 108 from the first flange 110. In this regard, the connecting rods 128 serve to provide a mechanical force tending to secure the top flange 110 to the top end of the transmission element 108 and the bottom flange 112 to the bottom end of the transmission element 108.

FIG. 1F illustrates a simplified schematic diagram of the plasma cell 102 equipped with one or more fins 129, in accordance with one or more embodiments of the present invention. In one embodiment, the one or more fins 129 (e.g., three fins or four fins) of the plasma cell 102 may serve to secure the one or more flanges 110, 112 at the openings 109*a*, 109*b*. In the case of a cylindrical transmission element 108, the fins 129 may be coupled to a first flange 110 and a second flange 110 positioned on the opposite end of the transmission element 108 from the first flange 110. In this regard, the fins 129, like the connecting rods 128, serve to provide a mechanical force tending to secure the top flange 110 to the top end of the transmission element 108 and the bottom flange 112 to the bottom end of the transmission element 108. It is further recognized that the fins 129 may be made suitably thin (and/or wedged) in order to limit obscuration between the illumination source 111 and the transmission element 108 and the transmission element 108 and the collection element 105. In another embodiment, the fins 129 are configured to cool the plasma cell 102 by transferring thermal energy from with the transmission element 108 to an ambient atmosphere (e.g., surrounding air). In another embodiment, the fins 129 may be configured to provide preload on the seals 114.

FIGS. 1G and 1H illustrate schematic view of the plasma cell 102, in accordance with one embodiment of the present invention. As shown in FIG. 1G, in addition to the various elements and features described previously herein, the plasma cell 102 further includes a mounting flange 130. As shown in FIGS. 1G and 1H, the top water cooling element 118 of the top flange 110 includes water cooling pipes for circulating water through the water cooling element 118. Further, as previously described herein, the bottom flange 112 includes a bottom water cooling element 120, which also includes water cooling pipes for circulating water through the water cooling element 120. In addition, the bottom flange 112 includes a gas inlet 122 used to fill (or empty) the transmission element 108. In another embodiment, the radiation shielding element 126 is disposed on the internal surface of the transmission element 108.

In one embodiment, system 100 may include various additional optical elements. In one embodiment, the set of additional optics may include collection optics configured to collect broadband illumination 115 emanating from the plasma 104. For instance, the system 100 may include a cold mirror 121 arranged to direct illumination from the collector element 105 to downstream optics, such as, but not limited to, a homogenizer 125.

In another embodiment, the set of optics may include one or more additional lenses (e.g., lens 117) placed along either the illumination pathway or the collection pathway of system 100. The one or more lenses may be utilized to focus illumination 113 from the illumination source 111 into the gas within volume 103. Alternatively, the one or more additional lenses may be utilized to focus broadband illumination 115 emanating from the plasma 104 onto a selected target (not shown).

In another embodiment, the set of optics may include a turning mirror 119. In one embodiment, the turning mirror 119 may be arranged to receive illumination 113 from the illumination source 111 and direct the illumination 113 to the gas within volume 103 contained within the transmission element 108 of the plasma cell 102 via collection element 105. In another embodiment, the collection element 105 is arranged to receive illumination from mirror 119 and focus the illumination to the focal point of the collection element 105 (e.g., ellipsoid-shaped collection element), where the transmission element 108 of the plasma cell 102 is located.

In another embodiment, the set of optics may include one or more filters 123 placed along either the illumination pathway or the collection pathway in order to filter illumination prior to light entering the transmission element 108 or to filter broadband illumination 115 following emission of the broadband illumination 115 from the plasma 104. It is noted herein that the set of optics of system 100 as described above and illustrated in FIG. 1A are provided merely for illustration and should not be interpreted as limiting. It is anticipated that a number of equivalent optical configurations may be utilized within the scope of the present invention.

It is contemplated herein that the system 100 may be utilized to sustain a plasma 104 in a variety of gas environments. In one embodiment, the gas used to initiate and/or maintain plasma 104 may include an inert gas (e.g., noble gas or non-noble gas) or a non-inert gas (e.g., mercury). In another embodiment, the gas used to initiate and/or maintain a plasma 104 may include a mixture of gases (e.g., mixture of inert gases, mixture of inert gas with non-inert gas or a mixture of non-inert gases). For example, it is anticipated herein that the gas within volume 103 used to generate a plasma 104 may include argon. For instance, the gas within volume 103 may include a substantially pure argon gas held at pressure in excess of 5 atm (e.g., 20-50 atm). In another instance, the gas within volume 103 may include a substantially pure krypton gas held at pressure in excess of 5 atm (e.g., 20-50 atm). In another instance, the within volume 103 may include a mixture of argon gas with an additional gas.

It is further noted that the present invention may be extended to a number of gases. For example, gases suitable for implementation in the present invention may include, but are not limited, to Xe, Ar, Ne, Kr, He, $N_2$, $H_2O$, $O_2$, $H_2$, $D_2$, $F_2$, $CH_4$, one or more metal halides, a halogen, Hg, Cd, Zn, Sn, Ga, Fe, Li, Na, Ar:Xe, ArHg, KrHg, XeHg, and the like. In a general sense, the present invention should be interpreted to extend to any light pump plasma generating system and should further be interpreted to extend to any type of gas suitable for sustaining a plasma within a plasma cell.

In another embodiment, the illumination source 111 of system 100 may include one or more lasers. In a general sense, the illumination source 111 may include any laser system known in the art. For instance, the illumination source 111 may include any laser system known in the art capable of emitting radiation in the infrared, visible or ultraviolet portions of the electromagnetic spectrum. In one embodiment, the illumination source 111 may include a laser system configured to emit continuous wave (CW) laser radiation. For example, the illumination source 111 may include one or more CW infrared laser sources. For example, in settings where the gas within volume 103 is or includes argon, the illumination source 111 may include a CW laser (e.g., fiber laser or disc Yb laser) configured to emit radiation at 1069 nm. It is noted that this wavelength fits to a 1068 nm absorption line in argon and as such is particularly useful for pumping argon gas. It is noted herein that the above description of a CW laser is not limiting and any laser known in the art may be implemented in the context of the present invention.

In another embodiment, the illumination source 111 may include one or more diode lasers. For example, the illumination source 111 may include one or more diode laser emitting radiation at a wavelength corresponding with any one or more absorption lines of the species of the gas contained within volume 103. In a general sense, a diode laser of the illumination source 111 may be selected for implementation such that the wavelength of the diode laser is tuned to any absorption line of any plasma (e.g., ionic transition line) or any absorption line of the plasma-producing gas (e.g., highly excited neutral transition line) known in the art. As such, the choice of a given diode laser (or set of diode lasers) will depend on the type of gas contained within the plasma cell 102 of system 100.

In another embodiment, the illumination source 111 may include an ion laser. For example, the illumination source 111 may include any noble gas ion laser known in the art. For instance, in the case of an argon-based plasma, the illumination source 111 used to pump argon ions may include an Ar+ laser.

In another embodiment, the illumination source 111 may include one or more frequency converted laser systems. For example, the illumination source 111 may include a Nd:YAG or Nd:YLF laser having a power level exceeding 100 Watts. In another embodiment, the illumination source 111 may include a broadband laser. In another embodiment, the illumination source 111 may include a laser system configured to emit modulated laser radiation or pulsed laser radiation.

In another embodiment, the illumination source 111 may include one or more non-laser sources. In a general sense, the illumination source 111 may include any non-laser light source known in the art. For instance, the illumination source 111 may include any non-laser system known in the art capable of emitting radiation discretely or continuously in the infrared, visible or ultraviolet portions of the electromagnetic spectrum.

In another embodiment, the illumination source 111 may include two or more light sources. In one embodiment, the illumination source 111 may include or more lasers. For example, the illumination source 111 (or illumination sources) may include multiple diode lasers. By way of another example, the illumination source 111 may include multiple CW lasers. In a further embodiment, each of the two or more lasers may emit laser radiation tuned to a different absorption line of the gas or plasma within the plasma cell 102 of system 100.

FIG. 2 is a flow diagram illustrating steps performed in a method 200 for forming a light-sustained plasma capable of emitting at least VUV radiation. Applicant notes that the embodiments and enabling technologies described previously herein in the context of system 100 should be interpreted to extend to method 200. It is further noted, however, that the method 200 is not limited to the architecture of system 100.

In a first step 202, illumination is generated. For example, as shown in FIG. 1A, an illumination source 111 may generate illumination 113 suitable for pumping a selected gas (e.g., argon, xenon, mercury and the like) to form a plasma 104. For instance, the illumination source 111 may include, but is not limited to, an infrared radiation source, a visible radiation source, or an ultraviolet radiation source.

In a second step 204, a volume of gas 103 is contained. For example, as shown in FIGS. 1A through 1H, a volume of gas 103 (e.g., argon, xenon, mercury and the like) is contained within the internal volume of the transmission element 108 by terminating the end(s) of the transmission element 108 with one or more flanges 110, 112.

In a third step 206, at least a portion of the generated illumination is focused through a transmission element 108 of the plasma cell 102 into the volume of gas 103 contained within the transmission element 108 of the plasma cell 102. For example, as shown in FIG. 1A, a collector element 105 having a generally ellipsoidal shape and an internal reflective surface may be arranged such that it directs illumination 113 from the illumination source 111 to a volume of gas 103 contained with the internal volume of the transmission element 108. In this regard, the transmission element 108 is at least partially transparent to a portion of the illumination 113 from the illumination source 111.

In a fourth step 208, broadband radiation including at least VUV radiation is generated. For example, broadband radiation including at least VUV radiation is generated by forming a plasma via absorption of the focused generated illumination by the volume of gas 103 contained within the internal volume of the transmission element 108 of plasma cell 102.

In a fifth step 210, at least a portion of the vacuum ultraviolet radiation is transmitted through the transmission element 108 of the plasma cell 102. For example, the transmission element 108 may be formed of a material at least partially transparent to at least a portion of the VUV radiation generated by the plasma 104. For instance, the transmission element 108 may be formed from $CaF_2$, $MgF_2$, sapphire, crystalline quartz, or fused silica.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected," or "coupled," to each other to achieve the desired functionality, and any two components capable of being so associated can also be viewed as being "couplable," to each other to achieve the desired functionality. Specific examples of couplable include but are not limited to physically mateable and/or physically interacting components and/or wirelessly interactable and/or wirelessly interacting components and/or logically interacting and/or logically interactable components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A system for forming a light-sustained plasma comprising:

an illumination source configured to generate illumination;

a plasma cell including a transmission element having a first opening and a second opening;

a first removable flange and a second removable flange attachable to the first opening and the second opening of the transmission element and configured to enclose the internal volume of the transmission element in order to contain a volume of gas within the plasma cell;

one or more fins external to the transmission element and coupled to the first flange and the second flange, the one or more fins configured to secure the first flange over the first opening and the second flange over the second opening, wherein the one or more fins transfer thermal energy from a portion of the plasma cell to an ambient atmosphere;

one or more internal control elements mechanically coupled to an internal surface of at least one of the one or more removable flanges, the one or more internal control elements including one or more protruding portions, the one or more protruding portions protruding into the volume of the transmission element beyond the internal surface of the at least one of the one or more removable flanges upon attachment of the one or more removable flanges to the one or more openings of the transmission element, wherein the one or more internal control elements are removable from the internal volume of the transmission element upon removal of the one or more removable flanges, wherein the one or more internal control elements include at least one of a temperature control device, a convection control device, a plume control device, a gas fill device or an ignition device; and a collector element arranged to focus the illumination from the illumination source into the volume of gas in order to generate a plasma within the volume of gas contained within the plasma cell, wherein the plasma emits broadband radiation including at least vacuum ultraviolet radiation, wherein the transmission element of the plasma cell is at least partially transparent to at least a portion of the illumination generated by the illumination source and at least a portion of the broadband radiation emitted by the plasma.

2. The system of claim 1, wherein the first opening and the second opening of the transmission element comprise:

a first opening at a first end of the transmission element; and a second opening at a second end of the transmission element opposite the first end.

3. The system of claim 1, wherein the transmission element has at least one of a substantially cylindrical shape and a substantially spherical shape.

4. The system of claim 1, wherein the transmission element has a composite shape.

5. The system of claim 1, wherein the temperature control device comprises:

at least one of an active temperature control device or a passive temperature control device.

6. The system of claim 1, wherein the convection control device comprises:

one or more flow control structures.

7. The system of claim 1, wherein the plume control device comprises:

a plume control device including a concave portion for at least one of capture or redirection of a plasma plume.

8. The system of claim 1, wherein the gas fill control device comprises:

at least one of a pipe or a tube.

9. The system of claim 1, wherein the ignition device comprises:

one or more electrodes.

10. The system of claim 1, further comprising:

one or more radiation shielding elements.

11. The system of claim 10, wherein the one or more radiation shielding elements comprise:

a radiation shield proximate to the one or more openings of the transmission element configured to block radiation from at least one of the illumination source and the radiation generated by the plasma from reaching one or more seals of the plasma cell.

12. The system of claim 1, further comprising:

a coating layer proximate to the one or more openings of the transmission element configured to block at least a portion of the radiation generated by the plasma from reaching one or more seals of the plasma cell.

13. The system of claim 1, wherein the transmission element of the plasma cell is at least partially transparent to radiation between 120 nm and 200 nm.

14. The system of claim 1, wherein the transmission element of the plasma cell is formed from at least one of calcium fluoride, magnesium fluoride, crystalline quartz, sapphire, and fused silica.

15. The system of claim 1, wherein broadband radiation emitted by the plasma further includes at least one of deep ultraviolet radiation, ultraviolet radiation, and visible radiation.

16. The system of claim 15, wherein the transmission element of the plasma cell is at least partially transparent to at least one of vacuum ultraviolet radiation, deep ultraviolet radiation, ultraviolet radiation, and visible radiation emitted by the plasma.

17. The system of claim 1, wherein the collector element is arranged to collect at least a portion of the broadband radiation emitted by the generated plasma and direct the broadband radiation to one or more additional optical elements.

18. The system of claim 1, wherein the collector element comprises:

an ellipsoid-shaped collector element.

19. The system of claim 1, wherein the illumination source comprises:

one or more lasers.

20. The system of claim 19, wherein the one or more lasers comprise:

one or more infrared lasers.

21. The system of claim 19, wherein the one or more lasers comprise:

at least one of a diode laser, a continuous wave laser, or a broadband laser.

22. The system of claim 1, wherein the gas comprises:

one or more inert gases.

23. The system of claim 1, wherein the gas comprises:

one or more non-inert gases.

24. The system of claim 1, wherein the gas comprises:

a mixture of two or more gases.

25. A system for forming a light-sustained plasma comprising:

an illumination source configured to generate illumination;

a plasma cell including a transmission element having one or more openings;

one or more removable flanges attachable to the one or more openings of the transmission element and configured to enclose the internal volume of the transmission element in order to contain a volume of gas within the plasma cell;

one or more fins external to the transmission element and coupled to the first flange and the second flange, the one or more fins configured to secure the first flange over the first opening and the second flange over the second opening, wherein the one or more fins transfer thermal energy from a portion of the plasma cell to an ambient atmosphere;

one or more control elements mechanically coupled to a surface of at least one of the one or more removable flanges, wherein the one or more control elements include at least one of a temperature control device, a convection control device, a plume control device, a gas fill device, or an ignition device; and a collector element arranged to focus the illumination from the illumination source into the volume of gas in order to generate a plasma within the volume of gas contained within the plasma cell, wherein the plasma emits broadband radiation, wherein the transmission element of the plasma cell is at least partially transparent to at least a portion of the illumination generated by the illumination source and at least a portion of the broadband radiation emitted by the plasma.

26. The system of claim 25, wherein broadband radiation emitted by the plasma includes at least one of vacuum ultraviolet radiation, deep ultraviolet radiation, ultraviolet radiation, and visible radiation.

27. The system of claim 25, wherein the transmission element of the plasma cell is at least partially transparent to at least one of vacuum ultraviolet radiation, deep ultraviolet radiation, ultraviolet radiation, and visible radiation emitted by the plasma.

28. The system of claim 25, wherein the collector element is arranged to collect at least a portion of the broadband radiation emitted by the generated plasma and direct the broadband radiation to one or more additional optical elements.

29. A plasma cell for forming a light-sustained plasma comprising:

a transmission element having a first opening and a second opening;

a first removable flange and a second removable flange attachable to the first opening and the second opening of the transmission element and configured to enclose the internal volume of the transmission element in order to contain a volume of gas within the plasma cell;

one or more fins external to the transmission element and coupled to the first flange and the second flange, the one or more fins configured to secure the first flange over the first opening and the second flange over the second opening, wherein the one or more fins transfer thermal energy from a portion of the plasma cell to an ambient atmosphere; and one or more internal control elements mechanically coupled to an internal surface of at least one of the one or more removable flanges, the one or more internal control elements including one or more protruding portions, the one or more protruding portions protruding into the volume of the transmission element beyond the internal surface of the at least one of the one or more removable flanges upon attachment of the one or more removable flanges to the one or more openings of the transmission element, wherein the one or more internal control elements are removable from the internal volume of the transmission element upon removal of the one or more removable flanges, wherein the one or more internal control elements include at least one of a temperature control device, a convection control device, a plume control device, a gas fill device, or an ignition device, the transmission element configured to receive illumination from an illumination source in order to generate a plasma within the volume of gas, wherein the plasma emits broadband radiation including at least vacuum ultraviolet (VUV) radiation, wherein the transmission element of the plasma cell is at least partially transparent to at least a portion of the illumination generated by the illumination source and at least a portion of the VUV radiation emitted by the plasma.

30. The plasma cell of claim 29, wherein the first opening and the second opening of the transmission element comprise:

a first opening at a first end of the transmission element; and a second opening at a second end of the transmission element opposite the first end.

31. The plasma cell of claim 29, wherein the transmission element has at least one of a substantially cylindrical shape and a substantially spherical shape.

32. The plasma cell of claim 29, wherein the transmission element has a composite shape.

33. The plasma cell of claim 29, further comprising:

one or more radiation shielding elements.

34. The plasma cell of claim 33, wherein the one or more radiation shielding elements comprise:

a radiation shield proximate to the one or more openings of the transmission element configured to block radiation from at least one of the illumination source and the radiation generated by the plasma from reaching one or more seals of the plasma cell.

35. The plasma cell of claim 29, further comprising:

a coating layer proximate to the one or more openings of the transmission element configured to block at least a portion of the radiation generated by the plasma from reaching one or more seals of the plasma cell.

36. The plasma cell of claim 29, wherein the transmission element is at least partially transparent to radiation between 120 nm and 200 nm.

37. The plasma cell of claim 29, wherein the transmission element is at least partially transparent to radiation between 190 nm and 260 nm.

38. The plasma cell of claim 29, wherein the transmission element is formed from at least one of calcium fluoride, magnesium fluoride, crystalline quartz, sapphire, and fused silica.

39. The plasma cell of claim 29, wherein broadband radiation emitted by the plasma further includes at least one of deep ultraviolet radiation, ultraviolet radiation, and visible radiation.

40. The plasma cell of claim 39, wherein the transmission element is at least partially transparent to at least one of deep ultraviolet radiation, ultraviolet radiation, and visible radiation.

41. The plasma cell of claim 29, wherein the illumination source comprises:

one or more lasers.

42. The plasma cell of claim 41, wherein the one or more lasers comprise:

one or more infrared lasers.

43. The plasma cell of claim 41, wherein the one or more lasers comprise:

at least one of a diode laser, a continuous wave laser, or a broadband laser.

44. The plasma cell of claim 29, wherein the gas comprises:

at least one of an inert gas, a non-inert gas, and a mixture of two or more gases.

45. A method for forming a light-sustained plasma comprising:

generating illumination;

containing a volume of gas within a plasma cell;

focusing at least a portion of the generated illumination through a transmission element of the plasma cell into the volume of gas contained within the plasma cell, the transmission element terminated with one or more removable flanges, wherein one or more internal control elements are mechanically coupled to an internal surface of at least one of the one or more removable flanges, the one or more internal control elements including one or more protruding portions, the one or more protruding portions protruding into the volume of the transmission element beyond the internal surface of the at least one of the one or more removable flanges upon attachment of the one or more removable flanges to the one or more openings of the transmission element;

one or more fins external to the transmission element and coupled to the one or more removable flanges, the one or more fins configured to secure the one or more removable flanges to the transmission element, wherein the one or more fins transfer thermal energy from a portion of the plasma cell to an ambient atmosphere;

generating broadband radiation including at least vacuum ultraviolet radiation by forming a plasma via absorption of the focused generated illumination by at least a portion of the volume of gas contained within the plasma cell; and transmitting at least a portion of the vacuum ultraviolet radiation through the transmission element of the plasma cell.

46. A system for forming a light-sustained plasma comprising: an illumination source configured to generate illumination; a plasma cell including a transmission element having one or more openings; one or more removable flanges attachable to the one or more openings of the transmission element and configured to enclose the internal volume of the transmission element in order to contain a volume of gas within the plasma cell; one or more internal plume control elements, wherein the one or more internal plume control elements include one or more concave structures including one or more central peaks, wherein the one or more internal plume control elements are mechanically coupled to an internal surface of the one or more removable flanges, one or more protruding portions protruding into the volume of the transmission element upon attachment of the one or more removable flanges to the one or more openings of the transmission element; one or more external temperature control devices mechanically coupled to an external surface of at least one of the one or more removable flanges; and a collector element arranged to focus the illumination from the illumination source into the volume of gas in order to generate a plasma within the volume of gas contained within the plasma cell, wherein the plasma emits broadband radiation including at least vacuum ultraviolet radiation, wherein the transmission element of the plasma cell is at least partially transparent to at least a portion of the illumination generated by the illumination source and at least a portion of the broadband radiation emitted by the plasma.

* * * * *